United States Patent
Bickers et al.

(10) Patent No.: US 6,770,594 B2
(45) Date of Patent: Aug. 3, 2004

(54) HERBICIDAL COMPOSITIONS

(75) Inventors: Udo Bickers, Wietmarschen (DE); Hermann Bieringer, Eppstein (DE); Gerhard Frisch, Wehrheim (DE); Erwin Hacker, Hochheim (DE); Hans Philipp Huff, Eppstein (DE)

(73) Assignee: Aventis CropScience, Frankfurt (DE)

( * ) Notice: Subject to any disclaimer, the term of this patent is extended or adjusted under 35 U.S.C. 154(b) by 0 days.

(21) Appl. No.: 09/911,072

(22) Filed: Jul. 23, 2001

(65) Prior Publication Data

US 2002/0058591 A1 May 16, 2002

(30) Foreign Application Priority Data

Jul. 25, 2000 (DE) .......................................... 100 36 002

(51) Int. Cl.⁷ .......................... A01N 25/00; A01N 47/36
(52) U.S. Cl. ........................ 504/212; 504/214; 504/363
(58) Field of Search ............................. 504/212, 214, 504/363, 215

(56) References Cited

U.S. PATENT DOCUMENTS

| 4,441,917 A | * | 4/1984 | Griffin et al. ................. 71/103 |
| 4,632,693 A |   | 12/1986 | Hillemann ..................... 71/93 |
| 5,424,072 A |   | 6/1995 | Narayanan et al. .......... 424/407 |

FOREIGN PATENT DOCUMENTS

| DE | 3636994 | 5/1987 |
| EP | 0 402 770 | 12/1990 |
| JP | 58-124702 | * 7/1983 |
| JP | 6-48902 | * 2/1994 |
| JP | 11-302116 | * 11/1999 |
| WO | WO 89/02570 | 2/1989 |
| WO | WO 89/02700 | 4/1989 |
| WO | WO 89/12394 | 12/1989 |
| WO | WO 91/15478 | 10/1991 |
| WO | WO 93/22919 | 11/1993 |
| WO | WO 93/25074 | 12/1993 |
| WO | WO 95/02327 | 1/1995 |
| WO | WO 96/00010 | 1/1996 |
| WO | WO 98/49894 | 11/1998 |

OTHER PUBLICATIONS

Adjuvants for Agrichemicals, Chapter 25, Matsumoto et al, "Effect of Humectants on Pesticide Uptake Through Plant Leaf Surfaces", pp. 261–271, 1992.
5–Agrochemicals; vol. 115; 1991; pp., "Effect of Humectants on the Pesticide Uptake Through Plant Leaf Surfaces", pp. 303–304, CA Abstract 115:250341n.
"Method of Controlling Aquatic Vegetation", Dec. 1981, also referred to as XP 001022458.
Database WPI, Section Ch, Week 199330, Class C02, AN 1993–239884, Jun. 1993, also referred to as XP 002182896; abstract of JP 5–163106A.
S. Matsumoto et al, "Effect of Humectants on Pesticide Uptake Through Plant Leaf Surfaces", *Adjuvants for Agrochemicals*, 1992, also referred to as XP 001022459.
Cook et al, "Uptake of Aminotriazole from Humectant–Surfactant Combinations and the Influence of Humidity", 1978, also referred to as XP 001022485.

* cited by examiner

*Primary Examiner*—S. Mark Clardy
(74) *Attorney, Agent, or Firm*—Frommer Lawrence & Haug LLP

(57) ABSTRACT

The present invention relates to a herbicidal composition comprising
a) one or more herbicidal active substances,
b) one or more surfactants other than silicone surfactants, and
c) one or more humectants.

The composition according to the invention is outstandingly suitable for controlling a variety of harmful plants.

25 Claims, No Drawings

HERBICIDAL COMPOSITIONS

The invention lies in the technical field of crop protection products, in particular active substance/surfactant/humectant combinations.

To control undesired harmful plants, a multiplicity of herbicides is available to the user, which can be employed as a function of the biological properties of the herbicides, the species of harmful plants to be controlled and the crop plant species. In this context, the herbicidal active substances are formulated in such a way that their application is as optimal as possible and that they have high activity. A variety of formulation auxiliaries such as wetters, dispersants, emulsifiers, antifoams, solvents or fillers are employed for this purpose.

However, the reliability and the level of the control of the harmful plants vary as a function of environmental factors such as temperature, atmospheric humidity, soil moisture, light incidence, precipitation or soil type, which can lead to follow-up treatments in the event of poor activity or to the damage of useful plants in the case of unduly high rates of application.

A more reliable activity also has ecological advantages. To avoid poor activity, the user frequently increases the amount of active substance to be applied. However, the disadvantage of this procedure is that the active substances' potential to affect soil fauna, to leach from the soil or to enter surface waters increases.

The effect of humectants on a variety of pesticides is described in Adjuvants for Agrochemicals, CRC Press, Inc. (1992), pp. 261–271. WO 89/02570 discloses that humectants in conjunction with certain silicone surfactants can increase the activity of herbicides.

The object of the present invention was to provide a herbicidal composition with improved level of action and improved reliability of action. This object is achieved by a specific herbicidal composition comprising herbicidal active substances in combination with certain surfactants and humectants.

The present invention thus relates to a herbicidal composition comprising
a) one or more herbicidal active substances,
b) one or more surfactants other than silicone surfactants, and
c) one or more humectants.

The herbicidal active substances a) which are present in the herbicidal compositions according to the invention are, for example, ALS inhibitors (acetolactate synthetase inhibitors) or herbicides other than ALS inhibitors, such as herbicides from the group of the carbamates, thiocarbamates, haloacetanilides, substituted phenoxy-, naphthoxy- and phenoxyphenoxycarboxylic acid derivatives and heteroaryloxyphenoxyalkanecarboxylic acid derivatives such as quinolyloxy-, quinoxalyloxy-, pyridyloxy-, benzoxazolyloxy- and benzothiazolyloxyphenoxyalkanecarboxylic acid esters, cyclohexanedione derivatives, imidazolinones, phosphorus-containing herbicides, for example of the glufosinate type or of the glyphosate type, pyrimidinyloxypyridinecarboxylic acid derivatives, pyrimidyloxybenzoic acid derivatives, triazolopyrimidinesulfonamide derivatives and S-(N-aryl-N-alkylcarbamoylmethyl) dithiophosphoric acid esters.

The ALS inhibitors are in particular sulfonamides, preferably from the group of the sulfonylureas, especially preferably those of the formula (I) and/or their salts $$R^a\text{—}SO_2\text{—}NR^b\text{—}CO\text{—}(NR^c)_x\text{—}R^d \qquad (I)$$

in which
$R^a$ is a hydrocarbon radical, preferably an aryl radical such as phenyl, which is unsubstituted or substituted or a heterocyclic radical, preferably a heteroaryl radical such as pyridyl, which is unsubstituted or substituted, and where the radicals including substituents have 1–30 carbon atoms, preferably 1–20 carbon atoms, or $R^a$ is an electron-attracting group such as a sulfonamide radical,
$R^b$ is a hydrogen atom or a hydrocarbon radical which is unsubstituted or substituted and including substituents has 1–10 carbon atoms, for example unsubstituted or substituted $C_1$–$C_6$-alkyl, preferably a hydrogen atom or methyl,
$R^c$ is a hydrogen atom or a hydrocarbon radical which is unsubstituted or substituted and including substituents has 1–10 carbon atoms, for example unsubstituted or substituted $C_1$–$C_6$-alkyl, preferably a hydrogen atom or methyl,
x equals zero or 1 and
$R^d$ is a heterocyclic radical.

Especially preferred ALS inhibitors are sulfonylureas of the formula (II) and/or their salts

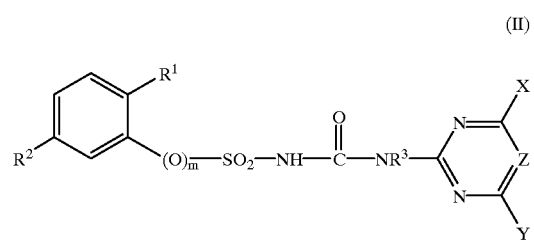

in which
$R^1$ is $C_1$–$C_4$-alkoxy, preferably $C_2$–$C_4$-alkoxy, or CO—$R^a$, in which $R^a$ equals OH, $C_1$–$C_4$-alkoxy or $NR^bR^c$, in which $R^b$ and $R^c$ independently of one another are identical or different and are H or $C_1$–$C_4$-alkyl,
$R^2$ is halogen or $(A)_n$—$NR^dR^e$, in which n equals zero or 1, A is a group CR'R" in which R' and R" independently of one another are identical or different and are H or $C_1$–$C_4$-alkyl, $R^d$ equals H or $C_1$–$C_4$-alkyl and $R^e$ is an acyl radical such as formyl or $C_1$–$C_4$-alkylsulfonyl, and, in the event that $R^1$ equals $C_1$–$C_4$-alkoxy, preferably $C_2$–$C_4$-alkoxy, $R^2$ can also be H,
$R^3$ is H or $C_1$–$C_4$-alkyl,
m equals zero or 1, preferably zero,
X and Y independently of one another are identical or different and are $C_1$–$C_6$-alkyl, $C_1$–$C_6$-alkoxy or $C_1$–$C_6$-alkylthio, where each of the three abovementioned radicals is unsubstituted or substituted by one or more radicals selected from the group consisting of halogen, $C_1$–$C_4$-alkoxy and $C_1$–$C_4$-alkylthio, or are $C_3$–$C_6$-cycloalkyl, $C_2$–$C_6$-alkenyl, $C_2$–$C_6$-alkynyl, $C_3$–$C_6$-alkenyloxy or $C_3$–$C_6$--alkynyloxy, preferably $C_1$–$C_4$-alkyl or $C_1$–$C_4$-alkoxy, and
Z equals CH or N.

Preferred sulfonylureas of the formula (II) and/or their salts are those in which
m equals zero and
a) $R^1$ equals CO—($C_1$–$C_4$-alkoxy) and $R^2$ equals halogen, preferably iodine, or $R^2$ equals $CH_2$—$NHR^e$, in which $R^e$ is an acyl radical, preferably $C_1$–$C_4$-alkylsulfonyl, or
b) $R^1$ equals CO—N($C_1$–$C_4$-alkyl)$_2$ and $R^2$ equals $NHR^e$, in which $R^e$ is an acyl radical, preferably formyl.

A hydrocarbon radical for the purposes of this description is a straight-chain, branched or cyclic and saturated or unsaturated aliphatic or aromatic hydrocarbon radical, for example alkyl, alkenyl, alkynyl, cycloalkyl, cycloalkenyl or aryl; aryl in this context is a mono-, bi- or polycyclic aromatic system, for example phenyl, naphthyl, tetrahydronaphthyl, indenyl, indanyl, pentalenyl, fluorenyl and the like, preferably phenyl. A hydrocarbon radical preferably has 1 to 40 carbon atoms, by preference 1 to 30 carbon atoms; especially preferably, a hydrocarbon radical is alkyl, alkenyl or alkynyl, each of which has up to 12 carbon atoms, or cycloalkyl having 3, 4, 5, 6 or 7 ring atoms, or phenyl.

A heterocyclic radical or ring (heterocyclyl) for the purposes of the present description can be saturated, unsaturated or heteroaromatic and unsubstituted or substituted; by preference, it contains one or more hetero atoms in the ring, by preference selected from the group consisting of N, O and S; it is by preference an aliphatic heterocyclyl radical having 3 to 7 ring atoms or a heteroaromatic radical having 5 or 6 ring atoms and contains 1, 2 or 3 hetero atoms. The heterocyclic radical can be, for example a heteroaromatic radical or ring (heteroaryl) such as, for example, a mono-, bi- or polycyclic aromatic system in which at least 1 ring contains one or more hetero atoms, for example pyridyl, pyrimidinyl, pyridazinyl, pyrazinyl, triazinyl, thienyl, thiazolyl, oxazolyl, furyl, pyrrolyl, pyrazolyl and imidazolyl, or is a partially or fully hydrogenated radical such as oxiranyl, oxetanyl, pyrrolidyl, piperidyl, piperazinyl, dioxolanyl, morpholinyl, tetrahydrofuryl. Suitable substituents for a substituted heterocyclic radical are the substituents given further below, and additionally also oxo. The oxo group can also be present on those hetero ring atoms which can exist in various oxidation numbers, for example in the case of N and S.

Substituted radicals for the purposes of the present description, such as substituted hydrocarbon radicals, for example substituted alkyl, alkenyl, alkynyl or aryl such as phenyl and benzyl, or substituted heterocyclyl, are, for example, a substituted radical which is derived from the unsubstituted skeleton, the substituents being, for example, one or more, preferably 1, 2 or 3, radicals selected from the group consisting of halogen (fluorine, chlorine, bromine, iodine), alkoxy, haloalkoxy, alkylthio, hydroxyl, amino, nitro, carboxyl, cyano, azido, alkoxycarbonyl, alkylcarbonyl, formyl, carbamoyl, mono- and dialkylaminocarbonyl, substituted amino such as acylamino, mono- and dialkylamino, and alkylsulfinyl, haloalkylsulfinyl, alkylsulfonyl, haloalkylsulfonyl and, in the case of cyclic radicals, also alkyl and haloalkyl, and unsaturated aliphatic radicals which correspond to the abovementioned saturated hydrocarbon-containing radicals, such as alkenyl, alkynyl, alkenyloxy, alkynyloxy and the like. In the case of radicals with carbon atoms, those having 1 to 4 carbon atoms, in particular 1 or 2 carbon atoms, are preferred. Preferred are, as a rule, substituents selected from the group consisting of halogen, for example fluorine and chlorine, ($C_1$–$C_4$)alkyl, preferably methyl or ethyl, ($C_1$–$C_4$) haloalkyl, preferably trifluoromethyl, ($C_1$–$C_4$)alkoxy, preferably methoxy or ethoxy, ($C_1$–$C_4$)haloalkoxy, nitro and cyano.

An acyl radical for the purposes of the present description is the radical of an organic acid which formally arises by elimination of an OH group from the organic acid, for example the radical of a carboxylic acid and radicals of acids derived therefrom such as thiocarboxylic acid, optionally N-substituted iminocarboxylic acids, or the radicals of carbonic monoesters, optionally N-substituted carbamic acids, sulfonic acids, sulfinic acids, phosphonic acids or phosphinic acids.

An acyl radical is preferably formyl or acyl selected from the group consisting of CO—$R^x$, CS—$R^x$, CO—$OR^x$, CS—$OR^x$, CS—$SR^x$, $SOR^Y$ or $SO_2R^Y$, where $R^x$ and $R^Y$ are each a $C_1$–$C_{10}$-hydrocarbon radical such as $C_1$–$C_{10}$-alkyl or $C_6$–$C_{10}$-aryl, which hydrocarbon radical is unsubstituted or substituted, for example by one or more substituents selected from the group consisting of halogen, such as F, Cl, Br, I, alkoxy, haloalkoxy, hydroxyl, amino, nitro, cyano or alkylthio, or $R^X$ and $R^Y$ are aminocarbonyl, or aminosulfonyl, the two last-mentioned radicals being unsubstituted, N-monosubstituted or N,N-disubstituted, for example by substituents selected from the group consisting of alkyl or aryl.

Acyl is, for example, formyl, haloalkylcarbonyl, alkylcarbonyl such as ($C_1$–$C_4$)alkylcarbonyl, phenylcarbonyl, it being possible for the phenyl ring to be substituted, or alkyloxycarbonyl, such as ($C_1$–$C_4$) alkyloxycarbonyl, phenyloxycarbonyl, benzyloxycarbonyl, alkylsulfonyl, such as ($C_1$–$C_4$) alkylsulfonyl, alkylsulfinyl, such as $C_1$–$C_4$ (alkylsulfinyl), N-alkyl-1-iminoalkyl, such as N—($C_1$–$C_4$)-1-imino-($C_1$–$C_4$)alkyl and other radicals of organic acids.

The active substances from the group of the ALS inhibitors such as sulfonylureas which are present as component a) in the herbicidal compositions according to the invention are to be understood as meaning, for the purposes of the present invention, not only the neutral compounds, but always also their salts with inorganic and/or organic counterions.

Thus, for example, sulfonylureas can form salts in which the hydrogen of the —$SO_2$—NH— group is replaced by an agriculturally suitable cation. These salts are, for example, metal salts, in particular alkali metal salts or alkaline earth metal salts, in particular sodium and potassium salts, or else ammonium salts or salts with organic amines. Likewise, salt formation can be effected by addition of an acid onto basic groups, such as, for example, amino and alkylamino. Acids which are suitable for this purpose are strong inorganic and organic acids, for example HCl, HBr, $H_2SO_4$ or $HNO_3$.

Preferred ALS inhibitors are from the series of the sulfonylureas, for example pyrimidinyl- or triazinylaminocarbonyl[benzene-, pyridine-, pyrazole-, thiophene- and (alkylsulfonyl)alkylamino]sulfamides. Preferred as substituents on the pyrimidine ring or triazine ring are alkoxy, alkyl, haloalkoxy, haloalkyl, halogen or dimethylamino, it being possible for all substituents to be combined independently of one another. Preferred substituents in the benzene-, pyridine-, pyrazole-, thiophene- or (alkylsulfonyl)alkylamino moiety are alkyl, alkoxy, halogen such as F, Cl, Br or I, amino, alkylamino, dialkylamino, acylamino such as formylamino, nitro, alkoxycarbonyl, aminocarbonyl, alkylaminocarbonyl, dialkylaminocarbonyl, alkoxyaminocarbonyl, haloalkoxy, haloalkyl, alkylcarbonyl, alkoxyalkyl, alkylsulfonylaminoalkyl, (alkanesulfonyl) alkylamino. Examples of such suitable sulfonylureas are A1) Phenyl- and benzylsulfonylureas and related compounds, for example 1-(2-chlorophenylsulfonyl)-3-(4-methoxy-6-methyl-1,3,5-triazin-2-yl)urea (chlorsulfuron), 1-(2-ethoxycarbonylphenylsulfonyl)-3-(4-chloro-6-methoxypyrimidin-2-yl)urea (chlorimuron-ethyl), 1-(2-methoxyphenylsulfonyl)-3-(4-methoxy-6-methyl-1,3, 5-triazin-2-yl)urea (metsulfuron-methyl), 1-(2-chloroethoxyphenylsulfonyl)-3-(4-methoxy-6-methyl-1,3,5-triazin-2-yl)urea (triasulfuron), 1-(2-methoxycarbonylphenylsulfonyl)-3-(4,6-dimethylpyrimidin-2-y)urea (sulfumeturon-methyl), 1-(2-methoxycarbonylphenylsulfonyl)-3-(4-methoxy-6-methyl-1,3,5-triazin-2-yl)-3-methylurea (tribenuron-methyl), 1-(2-methoxycarbonylbenzylsulfonyl)-3-(4,6-dimethoxypyrimidin-2-yl)urea (bensulfuron-methyl),
1-(2-methoxycarbonylphenysulfonyl)-3-(4,6-bis-(difluoromethoxy)pyrimidin-2-yl)urea, (primisulfuron-methyl),
3-(4-ethyl-6-methoxy-1,3,5-triazin-2-yl)-1-(2,3-dihydro-1,1-dioxo-2-methylbenzo-[b]thiophen-7-sulfonyl)urea (EP-A 0 796 83),
3-(4-ethoxy-6-ethyl-1,3,5-triazin-2-yl)-1-(2,3-dihydro-1,1-dioxo-2-methylbenzo[b]-thiophen-7-sulfonyl)urea (EP-A 0 079 683),
3-(4-methoxy-6-methyl-1,3,5-triazin-2-yl)-1-(2-methoxycarbonyl-5-iodophenyl-sulfonyl)urea (iodosulfuron-methyl and its sodium salt, WO 92/13845),
DPX-66037, triflusulfuron-methyl (see Brighton Crop Prot. Conf.—Weeds—1995, p. 853),
CGA-277476, (see Brighton Crop Prot. Conf.—Weeds—1995, p. 79), methyl 2-[3-(4,6-dimethoxypyrimidin-2-yl)ureidosulfonyl]-4-methanesulfonamido-methylbenzoate (mesosulfuron-methyl and its sodium salt, WO 95/10507),
N,N-dimethyl-2-[3-(4,6-dimethoxypyrimidin-2-yl)ureidosulfonyl]-4-formylamino-benzamide (foramsulfuron and its sodium salt, WO 95/01344);

A2) Thienylsulfonylureas, for example
1-(2-methoxycarbonylthiophen-3-yl)-3-(4-methoxy-6-methyl-1,3,5-triazin-2-yl)urea (thifensulfuron-methyl);

A3) Pyrazolylsulfonylureas, for example
1-(4-ethoxycarbonyl-1-methylpyrazol-5-yl-sulfonyl)-3-(4,6-dimethoxypyrimidin-2-yl)urea (pyrazosulfuron-methyl);
methyl 3-chloro-5-(4,6-dimethoxypyrimidin-2-ylcarbamoylsulfamoyl)-1-methylpyrazole-4-carboxylate (EP-A 0 282 613);
methyl 5-(4,6-dimethylpyrimidin-2-yl-carbamoylsulfamoyl)-1-(2-pyridyl)pyrazole-4-carboxylate (NC-330, see Brighton Crop Prot. Conference 'Weeds' 1991, Vol. 1, p45 et seq.),
DPX-A8947, azimsulfuron, (see Brighton Crop Prot. Conf. 'Weeds' 1995, p. 65);

A4) Sulfone diamide derivatives, for example
3-(4,6-dimethoxypyrimidin-2-yl)-1-(N-methyl-N-methylsulfonylaminosulfonyl)urea (amidosulfuron) and its structural analogs (EP-A 0 131 258 and Z. Pfl. Krankh. Pfl. Schutz, Special Issue XII, 489–497 (1990));

A5) Pyridylsulfonylureas, for example
1-(3-N,N-dimethylaminocarbonylpyridin-2-ylsulfonyl)-3-(4,6-dimethoxypyrimidin-2-yl)urea (nicosulfuron),
1-(3-ethylsulfonylpyridin-2-ylsulfonyl)-3-(-(4,6-dimethoxypyrimidin-2-yl)urea (rimsulfuron),
methyl 2-[3-(4,6-dimethoxypyrimidin-2-yl)ureidosulfonyl]-6-trifluoromethyl-3-pyridinecarboxylate, sodium salt (DPX-KE 459, flupyrsulfuron, see Brighton Crop Prot. Conf. Weeds, 1995, p. 49),
pyridylsulfonylureas as are described, for example in DE-A 40 00 503 and DE-A 40 30 577, preferably those of the formula

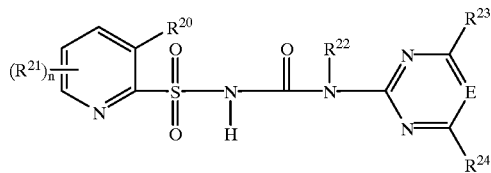

in which
E is CH or N, preferably CH,
$R^{20}$ is iodine or $NR^{25}R^{26}$,
$R^{21}$ is hydrogen, halogen, cyano, $(C_1-C_3)$alkyl, $(C_1-C_3)$alkoxy, $(C_1-C_3)$haloalkyl, $(C_1-C_3)$haloalkoxy, $(C_1-C_3)$alkylthio, $(C_1-C_3)$alkoxy$(C_1-C_3)$alkyl, $(C_1-C_3)$-alkoxycarbonyl, mono- or di$((C_1-C_3)$alkyl)amino, $(C_1-C_3)$alkylsulfinyl or sulfonyl, $SO_2-NR^xR^y$ or $CO-NR^xR^y$, in particular hydrogen,
$R^x$, $R^y$ independently of one another are hydrogen, $(C_1-C_3)$alkyl, $(C_1-C_3)$alkenyl, $(C_1-C_3)$alkynyl or together are $-(CH_2)_4-$, $-(CH_2)_5-$ or $-(CH_2)_2-O-(CH_2)_2-$,
n is 0,1,2 or 3, preferably 0 or 1,
$R^{22}$ is hydrogen or $CH_3$,
$R^{23}$ is halogen, $(C_1-C_2)$alkyl, $(C_1-C_2)$alkoxy, $(C_1-C_2)$haloalkyl, in particular $CF_3$, $(C_1-C_2)$haloalkoxy, preferably $OCHF_2$ or $OCH_2CF_3$,
$R^{24}$ is $(C_1-C_2)$alkyl, $(C_1-C_2)$haloalkoxy, preferably $OCHF_2$, or $(C_1-C_2)$alkoxy,
$R^{25}$ is $(C_1-C_4)$alkyl,
$R^{26}$ is $(C_1-C_4)$alkylsulfonyl or
$R^{25}$ and $R^{26}$ together are a chain of the formula $-(CH_2)_3SO_2-$ or $-(CH_2)_4SO_2-$, for example 3-(4,6-dimethoxypyrimiden-2-yl)-1-(3-N-methylsulfonyl-N-methylaminopyridin-2-yl)sulfonylurea, or their salts;

A6) Alkoxyphenoxysulfonylureas as are described, for example, in EP-A 0 342 569, preferably those of the formula

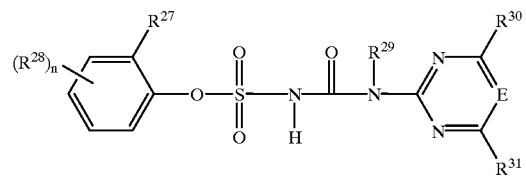

in which
E is CH or N, preferably CH,
$R^{27}$ is ethoxy, propoxy or isopropoxy,
$R^{28}$ halogen, $NO_2$, $CF_3$, CN, $(C_1-C_4)$alkyl, $(C_1-C_4)$alkoxy, $(C_1-C_4)$alkylthio or $(C_1-C_3)$alkoxy)carbonyl, preferably in the 6-position on the phenyl ring,
n is 0, 1, 2 or 3, preferably 0 or 1,
$R^{29}$ is hydrogen, $(C_1-C_4)$alkyl or $(C_3-C_4)$alkenyl,
$R^{30}$, $R^{31}$ independently of one another are halogen, $(C_1-C_2)$alkyl, $(C_1-C_2)$alkoxy, $(C_1-C_2)$haloalkyl, $(C_1-C_2)$haloalkoxy or $(C_1-C_2)$alkoxy$(C_1-C_2)$alkyl, preferably $OCH_3$ or $CH_3$, for example 3-(4,6-dimethoxypyrimidin-2-yl)-1-(2-ethoxyphenoxy)sulfonylurea, or their salts;

A7) Imidazolylsulfonylureas, for example MON 37500, sulfosulfuron (see Brighton Crop Prot. Conf. 'Weeds', 1995, p. 57), and other related sulfonylurea derivatives and mixtures of these.

Typical representatives of these active substances are, inter alia, the compounds listed hereinbelow: amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flupyrsulfuron-methyl-sodium, halosulfuron-methyl, imazosulfuron, metsulfuron-methyl, nicosulfuron, oxasulfuron, primisulfuron-methyl, prosulfuron, pyrazosulfuron-ethyl, rimsulfuron, sulfometuron-methyl, sulfosulfuron, thifensulfuron-methyl, triasulfuron, tribenuron-methyl, triflusulfuron-methyl, iodosulfuron-methyl and its sodium salt (WO 92/13845), mesosulfuron-methyl and its sodium salt (Agrow No. 347, Mar. 3, 2000, page 22 (PJB Publications Ltd. 2000)) and foramsulfuron and its sodium salt (Agrow No. 338, Oct. 15, 1999, page 26 (PJB Publications Ltd. 1999)).

The active substances listed hereinabove are known, for example, from "The Pesticide Manual", 12th Edition (2000), The British Crop Protection Council, or the references cited after the individual active substances.

The herbicidal active substances which are present in the herbicidal compositions according to the invention and which differ from the ALS inhibitors are, for example, herbicides from the group of the carbamates, thiocarbamates, haloacetanilides, substituted phenoxy-, naphthoxy- and phenoxyphenoxycarboxylic acid derivatives, and heteroaryloxyphenoxyalkanecarboxylic acid derivatives such as quinolyloxy-, quinoxalyloxy-, pyridyloxy-, benzoxazolyloxy- and benzothiazolyloxyphenoxyalkanecarboxylic esters, cyclohexanedione derivatives, imidazolinones, phosphorus-containing herbicides, for example of glufosinate type or of the glyphosate type, pyrimidinyloxypyridinecarboxylic acid derivatives, pyrimidyloxybenzoic acid derivatives, triazolopyrimidinesulfonamide derivatives and S-(N-aryl-N-alkylcarbamoylmethyl) dithiophosphoric esters. Preferred in this context are phenoxyphenoxy- and heteroaryloxyphenoxycarboxylic acid esters and salts, imidazolinones and herbicides such as bentazone, cyanazine, atrazine, dicamba or hydroxybenzonitriles such as bromoxynil and ioxynil and other foliar-acting herbicides.

Suitable herbicidal active substances a) which may be present as component a) in the herbicidal compositions according to the invention and which differ from the ALS inhibitors are, for example:

B) Herbicides of the phenoxyphenoxy- and heteroaryloxyphenoxycarboxylic acid derivatives type, such as B1) Phenoxyphenoxy- and benzyloxyphenoxycarboxylic acid derivatives, for example methyl 2-(4-(2,4-dichlorophenoxy)phenoxy)propionate (diclofop-methyl),
methyl 2-(4-(4-bromo-2-chlorophenoxy)phenoxy) propionate (DE-A 26 01 548),
methyl 2-(4-(4-bromo-2-fluorophenoxy)phenoxy) propionate (U.S. Pat. No. 4,808,750),
methyl 2-(4-(2-chloro-4-trifluoromethylphenoxy)phenoxy) propionate (DE-A 24 33 067),
methyl 2-(4-(2-fluoro-4-trifluoromethylphenoxy)phenoxy) propionate (U.S. Pat. No. 4,808,750),
methyl 2-(4-(2,4-dichlorobenzyl)phenoxy)propionate (DE-A 24 17 487),
ethyl 4-(4-(4-trifluoromethylphenoxy)phenoxy)pent-2-enoate,
methyl 2-(4-(4-trifluoromethylphenoxy)phenoxy) propionate (DE-A 24 33 067);

B2) "Mononuclear" heteroaryloxyphenoxyalkanecarboxylic acid derivatives, for example
ethyl 2-(4-(3,5-dichloropyridyl-2-oxy)phenoxy)propionate (EP-A 0 002 925),
propargyl 2-(4-(3,5-dichloropyridyl-2-oxy)phenoxy) propionate (EP-A 0 003 114),
methyl 2-(4-(3-chloro-5-trifluoromethyl-2-pyridyloxy) phenoxy)propionate (EP-A 0 003 890),
ethyl 2-(4-(3-chloro-5-trifluoromethyl-2-pyridyloxy) phenoxy)propionate (EP-A 0 003 890),
propargyl 2-(4-(5-chloro-3-fluoro-2-pyridyloxy)phenoxy) propionate (EP-A 0 191 736),
butyl 2-(4-(5-trifluoromethyl-2-pyridyloxy)phenoxy) propionate (fluazifop-butyl);

B3) "Binuclear" heteroaryloxyphenoxyalkanecarboxylic acid derivatives, for example
methyl and ethyl 2-(4-(6-chloro-2-quinoxalyloxy)phenoxy) propionate (quizalofopmethyl and quizalofopethyl),
methyl 2-(4-(6-fluoro-2-quinoxalyloxy)phenoxy)propionate (see J. Pest. Sci. Vol. 10, 61 (1985)),
2-isopropylideneaminooxyethyl 2-(4-(6-chloro-2-quinoxalyloxy)phenoxy)propionate (propaquizafop),
ethyl 2-(4-(6-chlorobenzoxazol-2-yloxy)phenoxy) propionate (fenoxaprop-ethyl), its D(+) isomer (fenoxaprop-P-ethyl) and ethyl 2-(4-(6-chlorobenzthiazol-2-yloxy)phenoxy)propionate (DE-A 26 40 730),
tetrahydro-2-furylmethyl 2-(4-(6-chloroquinoxalyloxy) phenoxy)propionate (EP-A 0 323 727);

C) Chloroacetanilides, for example
N-methoxymethyl-2,6-diethylchloroacetanilide (alachlor),
N-(3-methoxyprop-2-yl)-2-methyl-6-ethylchloroacetanilide (metolachlor),
2,6-dimethyl-N-(3-methyl-1,2,4-oxadiazol-5-ylmethyl) chloroacetanilide,
N-(2,6-dimethylphenyl)-N-(1-pyrazolylmethyl) chloroacetamide (metazachlor);

D) Thiocarbamates, for example
S-ethyl N,N-dipropylthiocarbamate (EPTC),
S-ethyl N,N-diisobutylthiocarbamate (butylate);

E) Cyclohexanedione oximes, for example
methyl 3-(1-allyloxyiminobutyl)4-hydroxy-6,6-dimethyl-2-oxocyclohex-3-enecarboxylate (alloxydim),
2-(1-ethoxyiminobutyl)-5-(2-ethylthiopropyl)-3-hydroxycyclohex-2-en-1-one (sethoxydim),
2-(1-ethoxyiminobutyl)-5-(2-phenylthiopropyl)-3-hydroxycyclohex-2-en-1-one (cloproxydim),
2-(1-(3-chloroallyloxy)iminobutyl)-5-(2-ethylthiopropyl)-3-hydroxycyclohex-2-en-1-one,
2-(1-(3-chloroallyloxy)iminopropyl)-5-(2-ethylthiopropyl)-3-hydroxycyclohex-2-en-1-one (clethodim),
2-(1-ethoxyiminobutyl)-3-hydroxy-5-(thian-3-yl)-cyclohex-2-enone (cycloxydim),
2-(1-ethoxyiminopropyl)-5-(2,4,6-trimethylphenyl)-3-hydroxycyclohex-2-en-1-one (tralkoxydim);

F) Imidazolinones, for example
methyl 2-(4-isopropyl-4-methyl-5-oxo-2-imidazolin-2-yl)-5-methylbenzoate and 2-(4-isopropyl-4-methyl-5-oxo-2-imidazolin-2-yl)-4-methylbenzoic acid (imazamethabenz),
5-ethyl-2-(4-isopropyl-4-methyl-5-oxo-2-imidazolin-2-yl) pyridine-3-carboxylic acid (imazethapyr),
2-(4-isopropyl-4-methyl-5-oxo-2-imidazolin-2-yl) quinoline-3-carboxylic acid (imazaquin),
2-(4-isopropyl-4-methyl-5-oxo-2-imidazolin-2-yl)pyridine-3-carboxylic acid (imazapyr),
5-methyl-2-(4-isopropyl-4-methyl-5-oxo-2-imidazolin-2-yl)pyridine-3-carboxylic acid (imazethamethapyr);

G) Triazolopyrimidinesulfonamide derivatives, for example
N-(2,6-difluorophenyl)-7-methyl-1,2,4-triazolo[1,5-c] pyrimidine-2-sulfonamide (flumetsulam),
N-(2,6-dichloro-3-methylphenyl)-5,7-dimethoxy-1,2,4-triazolo[1,5-c]pyrimidine-2-sulfonamide,
N-(2,6-difluorophenyl)-7-fluoro-5-methoxy-1,2,4-triazolo [1,5-c]pyrimidine-2-sulfonamide,
N-(2,6-dichloro-3-methylphenyl)-7-chloro-5-methoxy-1,2, 4-triazolo[1,5-c]pyrimidine-2-sulfonamide,
N-(2-chloro-6-methoxycarbonyl)-5,7-dimethyl-1,2,4-triazolo[1,5-c]pyrimidine-2-sulfonamide (EP-A 0 343 752, U.S. Pat. No. 4,988,812);

H) Benzoylcyclohexanediones, for example
2-(2-chloro-4-methylsulfonylbenzoyl)cyclohexane-1,3-dione (SC-0051, EP-A 0 137 963), 2-(2-nitrobenzoyl)-4, 4-dimethylcyclohexane-1,3-dione (EP-A 0 274 634),
2-(2-nitro-3-methylsulfonylbenzoyl)-4,4-dimethylcyclohexane-1,3-dione (WO 91/13548);

I) Pyrimidinyloxypyridinecarboxylic acid and pyrimidinyloxybenzoic acid derivatives, for example benzyl 3-(4,6-dimethoxypyrimidin-2-yl)oxypyridine-2-carboxylate (EP-A 0 249 707),
methyl 3-(4,6-dimethoxypyrimidin-2-yl)oxypyridine-2-carboxylate (EP-A 0 249 707),
2,6-bis[(4,6-dimethoxypyrimidin-2-yl)oxy]benzoic acid (EP-A 0 321 846),
1-(ethoxycarbonyloxyethyl) 2,6-bis[(4,6-dimethoxypyrimidin-2-yl)oxy]benzoate (EP-A 0 472 113);

J) S-(N-Aryl-N-alkylcarbamoylmethyl) dithiophosphonates such as S-[N-(4-chlorophenyl)-N-isopropylcarbamoylmethyl]O,O-dimethyl dithiophosphate (anilophos);

K) Alkylazines, for example as described in WO-A-97/08156, WO-A-97/31904, DE-A-19826670, WO-A-98/15536, WO-A-8/15537, WO-A-98/15538, WO-A-98/15539 and also DE-A-19828519, WO-A-98/34925, WO-A-98/42684, WO-A-99/18100, WO-A-99,19309, WO-A-99, 37627 and WO-A-99/65882, preferably those of the formula (E)

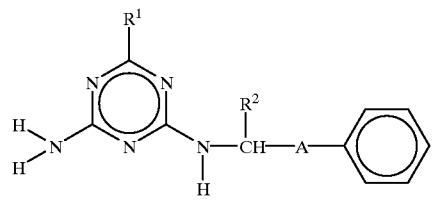
(E)

in which $R^1$ is $(C_1-C_4)$alkyl or $(C_1-C_4)$haloalkyl;
$R^2$ is $(C_1-C_4)$alkyl, $(C_3-C_6)$cycloalkyl or $(C_3-C_6)$cycloalkyl-$(C_1-C_4)$alkyl and
A is —$CH_2$—, —$CH_2$—$CH_2$—, —$CH_2$—$CH_2$—$CH_2$—, —O—, —$CH_2$—$CH_2$—O—, —$CH_2$—$CH_2$—$CH_2$—O—, especially preferably those of the formula E1–E7

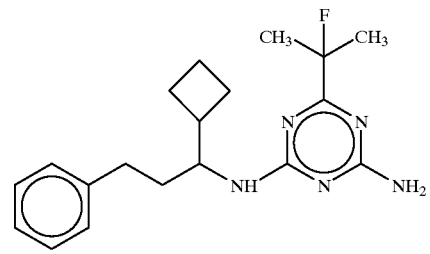
(E1)

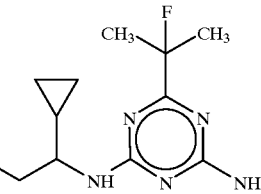
(E2)

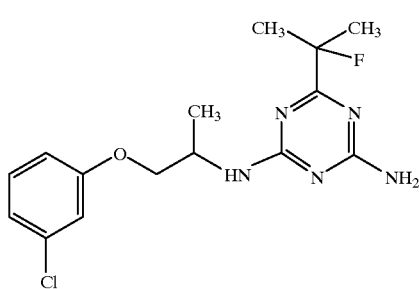
(E3)

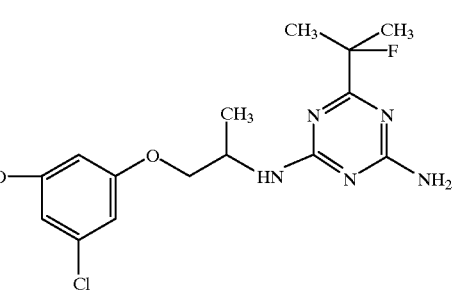
(E4)

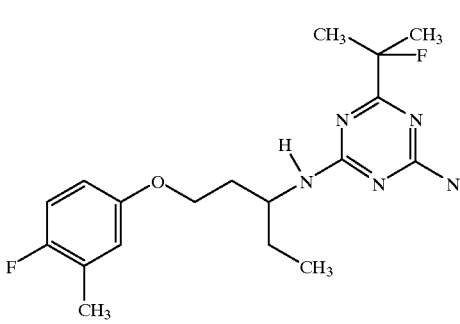
(E5)

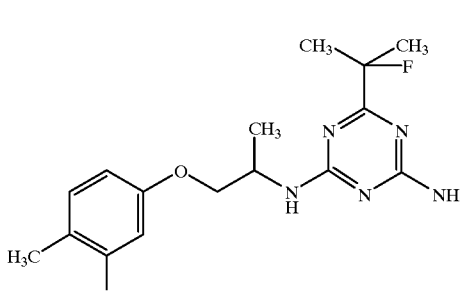
(E6)

(E7)

L) Phosphorus-containing herbicides, for example of the glufosinate type, such as glufosinate in the narrow sense, i.e. D,L-2-amino-4-[hydroxy(methyl)phosphinyl]-butanoic acid, glufosinatemonoammonium salts, L-glufosinate, L- or (2S)-2-amino-4-[hydroxy(methyl)phosphinyl]butanoic acid, L-glufosinate monoammonium salt or bialaphos (or bilanafos), i.e. L-2-amino-4-[hydroxy(methyl)phosphinyl]butanoyl-L-alanyl-L-alanine, in particular its sodium salt, or of the glyphosate type, such as glyphosate, i.e. N-(phosphonomethyl)glycine, glyphosate monoisopropylammonium salt, glyphosate sodium salt, or sulfosate, i.e. N-(phosphonomethyl)glycine trimesium salt=N-(phosphonomethyl)glycine trimethylsulfoxonium salt.

The herbicides of groups B to L are known, for example, from each of the specifications stated above and from "The Pesticide Manual", 12$^{th}$ Edition, 2000, The British Crop Protection Council, "Agricultural Chemicals Book II—Herbicides—", by W. T. Thompson, Thompson Publications, Fresno Calif., USA 1990 and "Farm Chemicals Handbook'90", Meister Publishing Company, Willoughby Ohio, USA, 1990.

The surfactants b) which are present in the herbicidal compositions according to the invention differ from silicone surfactants. Silicone surfactants are surfactants which contain at least one silicon atom and they are described, for example, in WO 89/12394. The surfactants present as surfactants b) in the herbicidal compositions according to the invention can be of the ionic and nonionic type, such as aromatic-based surfactants, for example surface-active benzenes or phenols which are substituted by one or more alkyl groups and have subsequently been derivatized, or nonaromatic-based surfactants, for example heterocycle-, olefin-, aliphatic- or cycloaliphatic-based surfactants, for example surface-active pyridine, pyrimidine, triazine, pyrrole, pyrrolidine, furan, thiophene, benzoxazole, benzothiazole and triazole compounds which are substituted by one or more alkyl groups and have subsequently been derivatized.

Examples of aromatic surfactants are:

b1) phenols, phenyl ($C_1$–$C_4$)alkyl ethers or (poly)alkoxylated phenols [=phenol (poly)alkylene glycol ethers], for example having 1 to 50 alkyleneoxy units in the (poly)alkyleneoxy moiety, where the alkylene moiety has preferably in each case 1 to 4 carbon atoms, preferably phenol which has been reacted with 3 to 10 mol of alkylene oxide, b2) (poly)alkylphenols or (poly)alkylphenol alkoxylates [=polyalkylphenol (poly)alkylene glycol ethers], for example having 1 to 12 carbon atoms per alkyl radical and 1 to 150 alkyleneoxy units in the polyalkyleneoxy moiety, preferably triisobutylphenol or tri-n-butylphenol which has been reacted with 1 to 50 mol of ethylene oxide, b3) polyarylphenols or polyarylphenol alkoxylates [=polyarylphenol (poly)alkylene glycol ethers], for example tristyrylphenol polyalkylene glycol ethers with 1 to 150 alkyleneoxy units in the polyalkyleneoxy moiety, preferably tristyrylphenol which has been reacted with 1 to 50 mol of ethylene oxide, b4) compounds which formally constitute the reaction products of the molecules described under b1) to b3) with sulfuric acid or phosphoric acid and their salts which have been neutralized with suitable bases, for example the acid phosphoric ester of the triethoxylated phenol, the acid phosphoric ester of a nonylphenol which has been reacted with 9 mol of ethylene oxide, and the triethanolamine-neutralized phosphoric acid ester of the reaction product of 20 mol of ethylene oxide and 1 mol of tristyrylphenol, and b5) acid (poly)alkyl- and (poly)arylbenzenesulfonates which have been neutralized with suitable bases, for example having 1 to 12 carbon atoms per alkyl radical, or having up to 3 styrene units in the polyaryl radical, preferably (linear) dodecylbenzenesulfonic acid and its oil-soluble salts such as, for example, the isopropylammonium salt of dodecylbenzenesulfonic acid.

In the case of the alkyleneoxy units, ethyleneoxy, propyleneoxy and butyleneoxy units, in particular ethyleneoxy units, are preferred.

Preferred surfactants from the group of the aromatic-based surfactants are, in particular, for example phenol which has been reacted with 4 to 10 mol of ethylene oxide, commercially available for example in the form of the Agrisol® brands (Akcros), triisobutylphenol which has been reacted with 4 to 50 mol of ethylene oxide, commercially available for example in the form of the Sapogenat®T brands (Clariant), nonylphenol which has been reacted with 4 to 50 mol of ethylene oxide, for example commercially available in the form of the Arkopal® brands (Clariant), tristyrylphenol which has been reacted with 4 to 150 mol of ethylene oxide, for example Soprophor®CY/8 (Rhodia), and acid (linear) dodecylbenzenesulfonate, for example commercially available in the form of the Marlon® brands (Hüls).

Examples of nonaromatic surfactants are given hereinbelow, where EO=ethylene oxide units, PO=propylene oxide units and BO=butylene oxide units:

b6) fatty alcohols having 10–24 carbon atoms with 0–60 EO and/or 0–20 PO and/or 0–15 BO in any desired sequence. The terminal hydroxyl groups of these compounds can be terminally capped by an alkyl, cycloalkyl or acyl radical having 1–24 carbon atoms. Examples of such compounds are:

Genapol®C,L,O,T,UD,UDD,X brands by Clariant, Plurafac® and Lutensol®A,AT,ON,TO brands by BASF, Marlipal®24 and O13 brands by Condea, Dehypon® brands by Henkel, Ethylan® brands by Akzo-Nobel such as Ethylan CD 120 or Synperonic® brands by Unichem, for example Synperonic® A7.

b7) Anionic derivatives of the products described under b6) in the form of ether carboxylates, sulfonates, sulfates and phosphates and their inorganic salts (for example alkali metal salts and alkaline earth metal salts) and organic salts (for example on an amine or alkanolamine base) such as Genapol®LRO, Sandopan® brands, Hostaphat/Hordaphos® brands by Clariant. Copolymers composed of EO,PO and/or BO units such as, for example, block copolymers such as the Pluronic® brands by BASF and the Synperonic® brands by Uniquema with a molecular weight of 400 to $10^8$. Alkylene oxide adducts of $C_1$–$C_9$ alcohols such as Atlox®5000 by Uniquema or Hoe® S3510 by Clariant.

Anionic derivatives of the products described under b8) and b9) in the form of ether carboxylates, sulfonates, sulfates and phosphates and their inorganic salts (for example alkali metal salts and alkaline earth metal salts) and organic salts (for example on an amine or alkanolamine base).

b8) Fatty acid and triglyceride alkoxylates such as the Serdox®NOG brands by Condea or the Emulsogen® brands by Clariant, salts of aliphatic, cycloaliphatic and olefinic carboxylic acids and polycarboxylic acids, and alpha-sulfofatty acid esters as available from Henkel.

b9) Fatty acid amide alkoxylates such as the Comperlan® brands by Henkel or the Amam® brands by Rhodia.

Alkylene oxide adducts of alkyne diols such as the Surfynol® brands by Air Products. Sugar derivatives such as amino and amido sugars from Clariant, glucitols from Clariant, alkyl polyglycosides in the form of the APG® brands by Henkel or such as sorbitan esters in the form of the Span® or Tween® brands by Uniquema or cyclodextrin esters or ethers from Wacker.

b10) Surface-active cellulose and algin, pectin and guar derivatives such as the Tylose® brands by Clariant, the Manutex® brands by Kelco and guar derivatives from Cesalpina.
Alkylene oxide adducts on a polyol base such as Polyglykol® brands by Clariant. Surface-active polyglycerides and their derivatives from Clariant.
b11) Sulfosuccinates, alkanesulfonates, paraffin- and olefinsulfonates such as Netzer IS®, Hoe®S1728, Hostapur®OS, Hostapur®SAS by Clariant, Triton®GR7ME and GR5 by Union Carbide, Empimin® brands by Albright and Wilson, Marlon®-PS65 by Condea.
b12) Sulfosuccinates such as the Aerosol® brands by Cytec or the Empimin® brands by Albright and Wilson.
b13) Alkylene oxide adducts of fatty amines, quaternary ammonium compounds with 8 to 22 carbon atoms ($C_8$–$C_{22}$) such as, for example, the Genamin®C,L,O,T brands by Clariant.
b14) Surface-active, zwitterionic compounds such as taurides, betaines and sulfobetaines in the form of Tegotain® brands by Goldschmidt, Hostapon®T and Arkopon®T brands by Clariant.
b15) Per- or polyfluorinated surface-active compounds such as Fluowet® brands by Clariant, the Bayowet® brands by Bayer, the Zonyl® brands by DuPont, and products of this type from Daikin and Asahi Glass.
b16) Surface-active sulfonamides, for example from Bayer.
b17) Surface-active polyacrylic and —methacrylic derivatives such as the Sokalan® brands by BASF.
b18) Surface-active polyamides such as modified gelatin or derivatized polyaspartic acid from Bayer and their derivatives.
b19) Surface-active polymers based on maleic anhydride and/or reaction products of maleic anhydride, and copolymers comprising maleic anhydride and/or reaction products of maleic anhydride, such as the Agrimer®VEMA brands by ISP.
b20) Surface-active derivatives of montan, polyethylene and polypropylene waxes such as the Hoechst® waxes or the Licowet® brands by Clariant.
b21) Surface-active phosphonates and phosphinates such as Fluowet®-PL by Clariant.
b22) Poly- or perhalogenated surfactants such as, for example, Emulsogen®-1557 by Clariant.

The surfactants b) which are present in the herbicidal compositions according to the invention are preferably of the type of the $C_8$–$C_{20}$-alkyl polyglycol ether sulfates, preferably $C_{10}$–$C_{18}$-alkyl polyglycol ether sulfates, which are preferably used in the form of their salts, for example alkali metal salts such as sodium salts or potassium salts, and/or ammonium salts, but also as alkaline earth metal salts such as magnesium salts, 2 to 5 ethylene oxide units preferably being present in the polyglycol moiety. An especially preferred example is sodium $C_{12}/C_{14}$-fatty alcohol diglycol ether sulfate (tradename for example Genapol® LRO, Clariant GmbH).

A humectant for the purposes of the present invention is understood as meaning a compound which is capable of physically absorbing water and/or storing water. Examples of preferred humectants are hygroscopic compounds.

Examples of substances which may be present in the herbicidal compositions according to the invention as humectant c) are the following:

$MgSO_4$, polyhydric alcohols such as ethylene glycol, propylene glycol, butanediol, glycerol and pentaerythritol, and their ethers and esters, for example ethylene, glycol ethers, propylene glycol ethers or glycerol esters; polyalkylene glycols such as polyethylene glycols (preferably with a molecular weight of 500–60000), polypropylene glycols (preferably with a molecular weight of 600–75000) and ethylene oxide (EO)/propylene oxide (PO) copolymers, for example with EO-PO-, EO-PO-EO- or PO-EO-PO units;
sugars such as hexoses, pentoses, molasses, alkylpolysaccharides and xanthans, for example the Malitol® brands by Salim Oleo Chemicals such as Maltitol® 75; gelatin; cellulose derivatives such as water-soluble lignosulfonates or hydroxycelluloses; citric acid and citric acid derivatives such as citric acid salts, for example alkali metal, alkaline earth metal or ammonium citrates, such as sodium citrate; lactic acid and lactic acid derivatives such as lactic acid salts, for example alkali metal, alkaline earth metal or ammonium lactates, such as sodium lactate, for example in the form of their racemates (DL) or of the individual optical isomers, for example sodium D-lactate and sodium L-lactate; tartaric acid and tartaric acid derivatives such as tartaric acid salts, for example alkali metal, alkaline earth metal or ammonium tartrates such as sodium tartrate, for example in the form of their racemates (uvic acid) or of the individual optical isomers, for example sodium (+)-tartrate and sodium (−)-tartrate; aspartic acid and aspartic acid derivatives such as aspartic acid salts, for example alkali metal, alkaline earth metal or ammonium aspartates such as sodium aspartate, for example in the form of their racemates (DL) or of the individual optical isomers, for example sodium D-aspartate and sodium L-aspartate; succinates such as the Triton® brands by Rohm and Haas; polyvinyl compounds such as modified polyvinylpyrrolidone such as the Luviskol® brands by BASF and the Agrimer® brands by ISP or the derivatized polyvinyl acetates such as the Mowilith® brands by Clariant or the polyvinyl butyrates such as the Lutonal® brands by BASF, the Vinnapas® and the Pioloform® brands by Wacker or the modified polyvinyl alcohols such as the Mowiol® brands by Clariant. Preferred humectants are polyhydric alcohols such as ethylene glycol or propylene glycol and lactic acid and lactic acid derivatives such as lactic acid salts, for example alkali metal, alkaline earth metal or ammonium lactates such as sodium lactate, for example in the form of their racemates (DL) or of the individual optical isomers, for example sodium D-lactate and sodium L-lactate.

The herbicidal compositions according to the invention conventionally comprise
a) 0.0001 to 99% by weight, preferably 0.1 to 95% by weight, of one or more herbicidal active substances,
b) 0.1 to 97% by weight of one or more surfactants other than silicone surfactants, and
c) 0.1 to 90% by weight of one or more humectants.

The herbicidal compositions according to the invention have an outstanding herbicidal activity. The improved control of the harmful plants by the herbicidal compositions according to the invention makes it possible to reduce the application rate and/or to increase the safety margin. Both make sense both from the economical and the ecological angle.

In a preferred embodiment, herbicidal compositions according to the invention are characterized by a synergistically active content for combination of the herbicides a) with surfactants b) and humectants c). In this context, it must be emphasized in particular that, as a rule, the herbicidal compositions of the invention have an inherent synergistic action, even in combinations with application rates or weight ratios of a):b):c) where synergism cannot be detected readily in each individual case, for example because the individual compounds are usually employed in very different application rates in the combination or else because even the individual compounds alone effect very good control of the harmful plants.

The herbicidal compositions according to the invention are prepared by customary processes, for example grinding, mixing, dissolving or dispersing individual components.

The components a), b) and c) of the herbicidal compositions according to the invention may be present together in a readymix which can then be applied in the customary fashion, for example in the form of a spray mixture, or they can be formulated separately and applied for example by the tank mix method or in succession. When the components are formulated separately, components a), b) and c) can be formulated for example in each case individually, or else components a) and b), a) and c) or b) and c) can be formulated jointly and the third component in each case is formulated separately.

The herbicidal compositions according to the invention can be formulated in various ways, depending on the prevailing biological and/or chemical-physical parameters. The following are examples of suitable formulation possibilities: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), oil- or water-based dispersions, oil-miscible solutions, capsule suspensions (CS), dusts (DP), seed-dressing materials, granules for spreading and soil application, granules (GR) in the form of microgranules, spray granules, coated granules and adsorption granules, water-dispersible granules (WG), water-soluble granules (SG), ULV formulations, microcapsules and waxes.

These individual formulation types are known in principle and are described, for example, in: Winnacker-Küchler, "Chemische Technologie" [Chemical Engineering], Volume 7, C. Hauser Verlag Munich, 4$^{th}$ Ed. 1986, Wade van Valkenburg, "Pesticide Formulations", Marcel Dekker, N.Y., 1973; K. Martens, "Spray Drying" Handbook, 3rd Ed. 1979, G. Goodwin Ltd. London.

The formulation auxiliaries required, such as inert materials, surfactants, solvents and additives, are also known and are described, for example, in Watkins, "Handbook of Insecticide Dust Diluents and Carriers", 2nd Ed., Darland Books, Caldwell N. J., H. v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesell., Stuttgart 1976; Winnacker-Küchler, "Chemische Technologie", Volume 7, C. Hauser Verlag Munich, 4$^{th}$ Ed. 1986.

Based on these formulations, it is also possible to prepare combinations with other agrochemical active substances such as insecticides, acaricides, herbicides, fungicides, safeners, fertilizers and/or growth regulators, for example in the form of a readymix or a tank mix.

Wettable powders are products which are uniformly dispersible in water and which, besides the herbicide a) and/or surfactant b) and/or humectant c), also comprise diluents or inert materials and, if appropriate further ionic and/or nonionic surfactants (wetters, dispersants), for example polyoxyethylated alkylphenols, polyoxethylated fatty alcohols, polyoxethylated fatty amines, fatty alcohol polyglycol ether sulfates, alkanesulfonates, alkylbenzenesulfonates, sodium lignosulfonates, sodium 2,2'-dinaphthylmethane-6,6'-disulfonate, sodium dibutyinaphthalene sulfonate or else sodium oleoylmethyltauride. To prepare the wettable powders, the herbicides a) and/or surfactants b) and/or humectants c) are ground finely, for example in customary apparatuses such as hammer mills, blower mills and air-jet mills, and mixed with the formulation auxiliaries, either simultaneously or subsequently. Emulsifiable concentrates are prepared by dissolving herbicide a) and/or surfactant b) and/or humectant c) in an organic solvent, for example butanol, cyclohexanone, dimethylformamide, xylene or else higher-boiling aromatics or hydrocarbons or mixtures of the organic solvents with addition of one or more ionic or nonionic surfactants (emulsifiers). Examples of emulsifiers which may be used are: calcium salts of alkylarylsulfonic acid, such as calcium dodecylbenzenesulfonate, or nonionic emulsifiers such as fatty acid polyglycol esters, alkylaryl polyglycol ethers, fatty alcohol polyglycol ethers, propylene oxide/ethylene oxide condensates, alkyl polyethers, sorbitan esters such as, for example, sorbitan fatty acid esters, or polyoxyethylene sorbitan esters such as, for example, polyoxyethylene sorbitan fatty acid esters.

Dusts are obtained by grinding herbicide a) and/or surfactant b) and/or humectant c) with finely divided solid materials, for example talc, natural clays such as kaolin, bentonite and pyrophyllite, or diatomaceous earth.

Suspension concentrates can be water- or oil-based. They can be prepared, for example by wet grinding by means of commercially available bead mills and, if appropriate, addition of further surfactants as have already been mentioned for example above in the case of the other formulation types.

Emulsions, for example oil-in-water emulsions (EW), can be prepared for example by means of stirrers, colloid mills and/or static mixers using aqueous organic solvents and, if appropriate, further surfactants as have already been mentioned for example above in the case of the other formulation types.

Granules can be prepared either by spraying the herbicide a) and/or surfactant b) and/or humectant c) onto adsorptive, granulated inert material or by applying active ingredient concentrates to the surface of carriers such as sand, kaolinites or granulated inert material with the aid of adhesives, for example polyvinyl alcohol, sodium polyacrylate or else mineral oils. Suitable herbicide a) and/or surfactant b) and/or humectant c) may also be granulated in the manner conventionally used for the production of fertilizer granules, if desired in a mixture with fertilizers. As a rule, water-dispersible granules are prepared by conventional processes such as spray drying, fluidized-bed granulation, disk granulation, mixing with high-speed mixers and extrusion without solid inert material. Regarding the production of disk granules, fluidized-bed granules, extruder granules and spray granules, see, for example, the methods in "Spray-Drying Handbook" 3rd Ed. 1979, G. Goodwin Ltd., London; J. E. Browning, "Agglomeration", Chemical and Engineering 1967, page 147 et seq; "Perry's Chemical Engineer's Handbook", 5th Ed., McGraw-Hill, New York 1973, pp. 8–57.

For further details on the formulation of crop protection products, see, for example, G. C. Klingman, "Weed Control as a Science", John Wiley and Sons, Inc., New York, 1961, pages 81–96 and J. D. Freyer, S. A. Evans, "Weed Control Handbook", 5th Ed., Blackwell Scientific Publications, Oxford, 1968, pages 101–103.

In addition, the abovementioned active ingredient formulations may comprise, if appropriate, additives such as adhesives, wetters, dispersants, emulsifiers, penetrants, preservatives, antifreeze agents, solvents, fillers, carriers, colorants, antifoams, evaporation inhibitors, pH regulators or viscosity regulators which are customary in each case.

The herbicidal compositions according to the invention can be used pre- or post-emergence, for example by spraying. The product input required for weed control can be reduced substantially by employing the herbicidal compositions according to the invention.

As a rule, the herbicides a) to be used in accordance with the invention are applied together with the surfactants b) and humectants c) or in succession, preferably in the form of a spray mixture comprising the herbicides a), the surfactants b) and the humectants c) in effective amounts and, if appropriate, further customary auxiliaries. The spray mixture is preferably prepared on the basis of water and/or an oil, for example a high-boiling hydrocarbon such as kerosene or paraffin. The herbicidal compositions according to the invention can be formulated as a tank mix or a readymix.

The active ingredient concentration in wettable powders is, for example, approximately 10 to 90% by weight, the remainder to 100% by weight being composed of customary formulation constituents. In the case of emulsifiable concentrates, the active ingredient concentration may amount to approximately 1 to 90%, preferably 5 to 80% by weight. Formulations in the form of dusts comprise 1 to 30% by weight of active ingredient, preferably in most cases 5 to 20% by weight of active ingredient, sprayable solutions contain approximately 0.05 to 80%, preferably 2 to 50% by weight of active ingredient. In the case of water-dispersible granules, the active ingredient content depends partly on whether the active compound is present in liquid or solid form and on which granulation auxiliaries, fillers and the like are being used. The active ingredient content amounts to, for example, between 1 and 95% by weight, preferably to between 10 and 80% by weight in the case of the water-dispersible granules.

The amount of surfactant b) in concentrated formulations can naturally not be increased at will without adversely affecting the stability of the formulation. In the concentrated formulations, the weight ratio herbicide a): surfactant b) is generally 1000:1 to 1:10000, preferably 200:1 to 1:200; the weight ratio herbicide a): humectant c) is generally from 1000:1 to 1:10000, preferably 200:1 to 1:200; and the weight ratio of surfactant b): humectant c) is generally 1000:1 to 1:1000, preferably 200:1 to 1:200.

Upon application, the weight ratio herbicide a): surfactant b) is generally in the range of from 1000:1 to 1:100000, in particular 200:1 to 1:1000, depending on the efficacy of the herbicide in question. The weight ratio herbicide a): humectant c) is upon application in general in the range from 1000:1 to 1:100000, in particular 200:1 to 1:200 depending on the efficacy of the herbicide in question. The weight ratio surfactant b): humectant c) upon application is generally in the range of from 1000:1 to 1:1000, preferably 200:1 to 1:200.

Upon application, the concentration of herbicide a) is generally 0.0001 to 20% by weight, preferably 0.01 to 3% by weight, in the composition applied, for example the spray mixture, at an application rate of 5 to 4000 l/ha, preferably 100 to 600 l/ha. In general, the concentration of surfactant b) is 0.001 to 5% by weight, preferably 0.1 to 2.0% by weight, in particular 0.1 to 0.5% by weight, in the composition applied, for example the spray mixture, at an application rate of 5 to 4000 l/ha, preferably 100 to 600 l/ha. In general, the concentration of humectant c) is 0.001 to 20% by weight, preferably 0.01 to 5% by weight, of humectant c) in the composition applied, for example the spray mixture, at an application rate of 5 to 4000 l/ha, preferably 100 to 600 l/ha.

Preferably, the herbicidal compositions according to the invention additionally comprise water and if appropriate, organic solvents besides components a), b) and c) and are formulated in the form of an aqueous concentrated dispersion or emulsion or as a tank mix in the form of a dilute dispersion, emulsion or solution with a degree of dilution of up to that of the ready-to-use spray mixture. A herbicidal composition prepared as a tank mix and comprising, for use, the preferred amounts of herbicide a), surfactant b) and humectant c) is especially preferred.

Mixtures or coformulations with other active substances such as, for example, insecticides, acaricides, herbicides, fungicides, safeners, fertilizers and/or growth regulators are possible, if appropriate.

For use, concentrated formulations which are present in commercially available form are, if appropriate, diluted in the customary fashion, for example by means of water in the case of wettable powders, emulsifiable concentrates, dispersions and water-dispersible granules. Preparations in the form of dusts, spray granules, absorption granules, sprayable solutions and spray mixtures prepared as tank mixes are not conventionally diluted further with additional inert substances prior to use. However, it may be advantageous or necessary to add further amounts of surfactants b), humectant c) and/or other conventional auxiliaries, in particular self-emulsifying oils or liquid paraffins, to the spray mixtures.

The application rate required of the herbicides a) varies with the external conditions such as temperature, humidity and the nature of the herbicide used. It can vary within wide limits, for example between 0.001 and 10 kg/ha or more of active substance, but it is preferably between 0.005 and 5 kg/ha.

The herbicidal compositions according to the invention have an outstanding herbicidal activity against a broad spectrum of economically important monocotyledonous and dicotyledonous harmful plants. The active ingredients also act efficiently on perennial weeds which produce shoots from rhizomes, rootstocks or other perennial organs and which are difficult to control. In this context, it does not matter whether the substances are applied before sowing, pre-emergence or post-emergence. Specific examples may be mentioned of some representatives of the monocotyledonous and dicotyledonous weed flora which can be controlled by the herbicidal compositions according to the invention, without the enumeration being a restriction to certain species.

Examples of weed species on which the herbicidal compositions act efficiently are, from amongst the monocotyledonous weed species, Avena, Lolium, Alopecurus, Phalaris, Echinochloa, Digitaria, Setaria and Bromus species, such as *Bromus catharticus, Bromus secalinus, Bromus erectus, Bromus tectorum* and *Bromus japonicus,* and Cyperus species from the annual group, and, among the perennial species, Agropyron, Cynodon, Imperata and Sorghum and also perennial Cyperus species.

In the case of the dicotyledonous weed species, the spectrum of action extends to genera such as, for example, Galium, Viola, Veronica, Lamium, Stellaria, Amaranthus, Sinapis, Ipomoea, Matricaria, Abutilon and Sida amongst the annuals, and Convolvulus, Cirsium, Rumex and Artemisia in the case of the perennial weeds.

The active ingredients according to the invention also act outstandingly efficiently on harmful plants which are found under the specific cultures in rice, such as, for example, Echinochloa, Sagittaria, Alisma, Eleocharis, Scirpus and Cyperus.

If the herbicidal compositions according to the invention are applied to the soil surface before germination, the weed seedlings are either prevented completely from emerging or else the weeds grow until they have reached the cotyledon stage, but then their growth stops, and, eventually, after three to four weeks have elapsed, they die completely.

If the herbicidal compositions according to the invention are applied post-emergence to the green parts of the plants, growth likewise stops drastically a very short time after the treatment, and the weed plants remain at the growth stage of the point of time of application, or they die completely after a certain time, so that in this manner competition by the weeds, which is harmful to the crop plants, is eliminated very early and in a sustained manner.

Even though the herbicidal compositions according to the invention have an outstanding herbicidal activity against monocotyledonous and dicotyledonous weeds, crop plants of economically important crops such as dicotyledonous crops such as, for example, soybeans, cotton, oilseed rape, sugarbeet, in particular soybean, or graminaceous crops such as wheat, barley, rye, rice or maize, are harmed only to a minor extent, if at all. For these reasons, the present compounds are highly suitable for the selective control of undesired vegetation in stands of agriculturally useful plants or of ornamentals.

In addition, the herbicidal compositions according to the invention have outstanding growth-regulatory properties in crop plants. They engage in the plants' metabolism in a regulatory fashion and can thus be used for the directed control of plant constituents and for facilitating harvesting, such as, for example, by triggering desiccation and stunted growth. Moreover, they are also suitable for generally controlling and inhibiting undesired vegetative growth without destroying the plants in the process. Inhibition of the vegetative growth plays an important role in many monocotyledonous and dicotyledonous crops since lodging can be reduced, or prevented completely, thereby.

Owing to their herbicidal and plant-growth regulatory properties, the herbicidal combinations according to the invention can also be employed for controlling harmful plants in crops of genetically modified plants which are known or yet to be developed. As a rule, the transgenic plants are distinguished by particular advantageous properties, for example by resistances to certain pesticides, especially certain herbicides, resistances to plant diseases or to plant pathogens such as certain insects or microorganisms such as fungi, bacteria or viruses. Other particular properties concern for example the harvested material with regard to quantity, quality, storeability, composition and specific constituents. Thus, transgenic plants with an increased starch content or with a modified starch quality or with a different fatty acid composition of the harvested material are known.

The use of the compositions according to the invention in economically important transgenic crops of useful plants and ornamentals, such as graminaceous crops such as wheat, barley, rye, oats, millet, rice and maize or else crops of sugarbeet, cotton, soybean, oilseed rape, potato, tomato, pea and other vegetables is preferred. The compositions according to the invention may preferably be employed as herbicides in crops of useful plants which are resistant to the phytotoxic effects of the herbicides or which have been rendered resistant to the phytotoxic effects of the herbicides by recombinant means.

When the herbicidal compositions according to the invention are used in transgenic crops, effects are frequently observed—in addition to the effects on harmful plants which can be observed in other crops—which are specific for the application in the transgenic crop in question, for example a modified or specifically extended weed spectrum which can be controlled, also modified application rates which can be employed for application, preferably good combining properties with the herbicides to which the transgenic crop is resistant, and an effect on growth and yield of the transgenic crop plants.

A subject of the invention is therefore also the use of the compositions according to the invention as herbicides for controlling harmful plants, preferably in crops of plants, it also being possible for the crops of plants to take the form of crops of transgenic plants.

The herbicidal compositions according to the invention can also be employed nonselectively for controlling undesired vegetation, for example in plantation crops, on verges, squares, industrial terrain or rail tracks.

Owing to the relatively low application rate of the herbicidal compositions according to the invention, they are generally already very well tolerated. In particular, a reduction in the absolute application rate can be achieved by the combinations according to the invention, compared with the individual use of a herbicidal active substance.

A subject of the invention is therefore also a method of controlling harmful plants, preferably for selectively controlling harmful plants in crops of useful plants, which comprises applying a herbicidally active amount of the abovementioned herbicides a) in combination with at least one of the surfactants b) and at least one humectant c), for example pre-emergence, post-emergence or pre- and post-emergence, preferably pre-emergence, jointly or in succession, to the plants, plant parts, plant seeds or the area on which the plants grow, for example the area under cultivation.

In a preferred method variant, the herbicides a) are applied in application rates of from 0.1 to 2000 g of active substances/ha, preferably of from 0.5 to 1000 g of active substances/ha. It is furthermore especially preferred to apply the active ingredients in the form of a readymix or in the form of tank mixes, where the individual components, for example in the form of formulations, are jointly mixed with water in the tank and the resulting spray mixture is applied.

Since the crop plant compatibility of the combinations according to the invention is extremely good, combined with a very high degree of control of the harmful plants, the combinations according to the invention can be considered as selective. In a preferred embodiment, herbicidal compositions with the active substances combinations according to the invention are therefore employed for selectively controlling undesired plants.

If, if desired, the compatibility and/or selectivity of the herbicidal compositions according to the invention is to be increased even further, it may be advantageous to apply them together with safeners or antidotes, either jointly in a mixture or staggered in time.

Compounds which are suitable as safeners or antidotes for the herbicidal compositions according to the invention are known, for example, from EP-A-333 131 (ZA-89/1960), EP-A-269 806 (U.S. Pat. No. 4,891,057), EP-A-346 620 (AU-A-89/34951) and the international patent applications PCT/EP 90/01966 (WO-91108202) and PCT/EP 90102020 (WO-911078474) and literature cited therein or can be prepared by the processes described therein. Further suitable safeners are known from EP-A-94 349 (U.S. Pat. No. 4,902,304), EP-A-191 736 (U.S. Pat. No. 4,881,966) and EP-A-0 492 366 and the literature cited therein.

In a preferred embodiment, the herbicidal compositions of the present invention therefore contain an additional content of one or more compounds which act as safeners or antidotes.

Especially preferred antidotes or safeners or groups of compounds which are suitable as safeners or antidotes for the above-described herbicidal compositions of the invention are, inter alia:

a) compounds of the dichlorophenylpyrazolin-3-carboxylic acid type, preferably compounds such as ethyl 1-(2,4-dichlorophenyl)-5-(ethoxycarbonyl)-5-methyl-2-pyrazoline-3-carboxylate (compound S1-1, mefenpyr-diethyl) and related compounds as are described in the international application WO 91/07874 (PCT/EP 90102020);

b) dichlorophenylpyrazolecarboxylic acid derivatives, preferably compounds such as ethyl 1-(2,4-dichlorophenyl)-5-methylpyrazole-3-carboxylate (compound S1-2), ethyl 1-(2,4-dichlorophenyl)-5-isopropylpyrazole-3-carboxylate (compound S1-3), ethyl 1-(2,4-dichlorophenyl)-5-(1,1-dimethylethyl)pyrazole-3-carboxylate (compound S1-4), ethyl 1-(2,4-dichlorophenyl)-5-phenylpyrazole-3-carboxylate (compound S1-5) and related compounds as are described in EP-A-0 333 131 and EP-A-0 269 806;

c) compounds of the triazolecarboxylic acids type, preferably compounds such as ethyl 1-(2,4-dichlorophenyl)-5-trichloromethyl-(1H)-1,2,4-triazole-3-carboxylate (compound S1-6, fenchlorazole) and related compounds (see EP-A-0 174 562 and EP-A-0 346 620);

d) compounds of the dichlorobenzyl-2-isoxazoline-3-carboxylic acid type, compounds of the 5-benzyl- or 5-phenyl-2-isoxazoline-3-carboxylic acid type, preferably compounds such as ethyl 5-(2,4-dichlorobenzyl)-2-isoxazoline-3-carboxylate (compound S1-7) or ethyl 5-phenyl-2-isoxazoline-3-carboxylate (compound S1-8), and related compounds as are described in international patent application WO 91/08202 (PCT/EP 90/01966);

e) compounds of the 8-quinolinoxyacetic acid type, preferably compounds such as 1-methylhex-1-yl (5-chloro-8-quinolinoxy)acetate (S2-1; cloquintocet-mexyl),
1,3-dimethylbut-1-yl (5-chloro-8-quinolinoxy)acetate (S2-2),
4-allyloxy (5-chloro-8-quinolinoxy)acetate (S2-3),
1-allyloxy-prop-2-yl (5-chloro-8-quinolinoxy)acetate (S2-4),
ethyl (5-chloro-8-quinolinoxy)acetate (S2-5),
methyl (5-chloro-8-quinolinoxy)acetate (S2-6),
allyl (5-chloro-8-quinolinoxy)acetate (S2-7),
2-(2-propylideneiminoxy)-1-ethyl (5-chloro-8-quinolinoxy)acetate (S2-8),
2-oxoprop-1-yl (5-chloro-8-quinolinoxy)acetate (S2-9)
and related compounds as are described in EP-A-0 086 750, EP-A-0 094 349 and EP-A-0 191 736 or EP-A-0 492 366;

f) compounds of the (5-chloro-8-quinolinoxy)malonic acid type, preferably compounds such as diethyl (5-chloro-8-quinolinoxy)malonate, diallyl (5-chloro-8-quinolinoxy) malonate, methyl ethyl (5-chloro-8-quinolinoxy) malonate and related compounds as have been described and proposed in German patent application EP-A-0 582 198;

g) active substances of the type of the phenoxyacetic acid derivatives or phenoxypropionic acid derivatives or of the aromatic carboxylic acids such as, for example, 2,4-dichlorophenoxyacetic acid (and esters) (2,4-D), 4-chloro-2-methylphenoxypropionic acid (mecoprop), MCPA or 3,6-dichloro-2-methoxybenzoic acid (and esters) (dicamba).

h) compounds of the 5,5-diphenyl-2-isoxaoline-3-carboxylic acid type, preferably ethyl 5,5-diphenyl-2-isoxazoline-3-carboxylate (S3-1, isoxadifen-ethyl).

i) compounds which are known as safeners, for example for rice, such as fenclorim (=4,6-dichloro-2-phenylpyrimidine, Pesticide Manual, 11$^{th}$ Edition, 1997, pp. 511–512), dimepiperate (=S-1-methyl-1-phenylethyl piperidine-1-thiocarboxylate, Pesticide Manual, 11$^{th}$ Edition, 1997, pp. 404–405), daimuron (=1-(1-methyl-1-phenylethyl)-3-p-tolylurea, Pesticide Manual, 11$^{th}$ Edition, 1997, p. 330), cumyluron (=3-(2-chlorophenylmethyl)-1-(1-methyl-1-phenylethyl) urea, JP-A-60/087254), methoxyphenone (=3,3'-dimethyl-4-methoxybenzophenone, CSB (=1-bromo-4-(chloromethylsulfonyl)benzene, CAS-Reg. No. 54091-06-4).

In addition, at least some of the abovementioned compounds are described in EP-A-0 640 587, which is herewith referred to for disclosure purposes.

j) A further important group of compounds which are suitable as safeners and antidotes is known from WO 95107897.

The safeners (antidotes) of the above groups a) to j) reduce or prevent phytotoxic effects which may be observed when the herbicidal compositions according to the invention are employed in crops of useful plants, without adversely affecting the efficacy of the herbicides against harmful plants. This makes it possible considerably to widen the spectrum of application of the herbicidal compositions according to the invention; in particular, the use of safeners makes possible the application of herbicidal compositions which could previously only be employed to a limited extent or with insufficient success, i.e. of combinations which, at low dosages with a poor spectrum of action, led to insufficient control of the harmful plants without safener.

Components a), b) and c) of the herbicidal compositions according to the invention and the abovementioned safeners can be applied jointly (for example as readymix or by the tank mix method) or in succession in any desired sequence. The weight ratio safener:herbicide (compound(s) of the formula (I) and/or their salts) can vary within wide ranges and is preferably in the range of from 1:100 to 100:1, in particular of from 1:100 to 50:1. The amounts of herbicide (s) and safener(s) which are optimal in each case usually depend on the type of the herbicidal composition and/or on the safener used, and also on the nature of the plant stand to be treated.

Depending on their properties, the safeners can be used for pretreating the seed of the crop plant (seed dressing) or introduced into the seed furrows prior to sowing or applied together with the herbicide mixture before or after emergence of the plants. Pre-emergence treatment includes both the treatment of the area under cultivation before sowing and the treatment of the areas under cultivation where seed has been sown, but growth is as yet not present. The joint application with the herbicide mixture is preferred. Tank mixes or readymixes can be employed for this purpose.

The application rates required, of the safeners, can vary within wide limits, depending on the indication and the herbicide used; they are, as a rule, in the range of from 0.001 to 1 kg, preferably 0.005 to 0.2 kg, of active substance per hectare.

The herbicidal compositions according to the invention can be applied in the customary fashion, for example with water as carrier in spray mixture quantities of approximately 5 to 4000 liters/ha. Application of the compositions by what is known as the low-volume and ultra-low-volume methods (ULV) is also possible, as is their application in the form of granules and microgranules.

A preferred use relates to application of herbicidal compositions which contain components a), b) and c) in a synergistically active amount. The invention also extends to mixtures of one or more herbicides a) with one or more surfactants b) and one or more humectants c).

Besides, one, two or more of agrochemical active substances other than herbicide a) (for example herbicides, insecticides, fungicides, safeners) may be present in the herbicidal compositions of the invention for complementing the properties, usually in minor amounts.

This results in a large number of possibilities of combining several active substances with each other and of employing them jointly for controlling harmful plants in crops of plants without deviating from the spirit of the invention.

Thus, in a preferred embodiment, for example various active substances of the formula (II) and/or their salts may be combined with each other, for example
mesosulfuron-methyl+iodosulfuron-methyl,
mesosulfuron-methyl+iodosulfuron-methyl-sodium,
mesosulfuron-methyl+foramsulfuron,
mesosulfuron-methyl+foramsulfuron-sodium,
mesosulfuron-methyl-sodium+iodosulfuron-methyl,
mesosulfuron-methyl-sodium+iodosulfuron-methyl-sodium,
mesosulfuron-methyl-sodium+foramsulfuron,
mesosulfuron-methyl-sodium+foramsulfuron-sodium,
foramsulfuron+iodosulfuron-methyl,
foramsulfuron+iodosulfuron-methyl-sodium,
foramsulfuron-sodium+iodosulfuron-methyl,
foramsulfuron-sodium+iodosulfuron-methyl-sodium.

The herbicidal active substances a) and their mixtures, for example the abovementioned active substance mixtures of active substances of the formula (II) and/or their salts, can preferably be combined with a $C_8$–$C_{20}$-alkyl polyglycol ether sulfate such as sodium $C_{12}/C_{14}$-fatty alcohol diglycol ether sulfate (tradename for example Genapol® LRO, Clariant GmbH) as component b) and a lactic acid derivative such as sodium lactate as component c). In addition, preferably one or more safeners may be present, in particular the safeners mefenpyr-diethyl (S1-1), cloquintocet-mexyl (S2-1) and isoxadifen-ethyl (S3-1).

In conclusion, it can be said that the herbicidal compositions according to the invention have an outstanding herbicidal action and that in a preferred embodiment superadditive (=synergistic) effects are observed. In this case, the action in the combinations exceeds that of the individual components employed alone.

These effects permit inter alia a reduction in the application rate, control of a broader spectrum of broad-leaved weeds and grass weeds, filling in of gaps in action, a more rapid and more reliable action, a prolonged duration of action, complete control of harmful plants with only one or few applications, and a widened period of application. The abovementioned properties are required in weed control practice in order to keep agricultural crops free from undesired plant competitors and thus to safeguard and/or increase the yields in terms of quality and quantity. The technical standard is exceeded markedly by the combinations according to the invention with regard to the properties described. Thus, a considerably improved reliability of action is observed under different environmental conditions.

In a further embodiment of the present invention, herbicidal compositions comprising at least one compound of the formula (II') and/or their salts

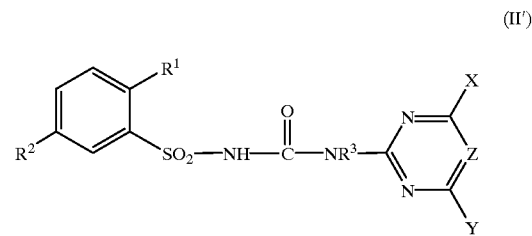

(II')

in which $R^1$ is CO—($C_1$–$C_4$-alkoxy), $R^2$ is $CH_2$—$NHR^e$, where $R^e$ is an acyl radical, preferably $C_1$–$C_4$-alkylsulfonyl, $R^3$ is H or $C_1$–$C_4$-alkyl, and X, Y and Z are as defined in formula (II), for example mesosulfuron-methyl and/or its salts such as the sodium salt, are outstandingly suitable for controlling Bromus species such as Bromus catharticus, Bromus secalinus, Bromus erectus, Bromus tectorum and Bromus japonicus.

Bromus plants are controlled particularly efficiently under normal conditions of humidity, and Bromus is still controlled under very dry conditions. Normal conditions of humidity are to be understood as meaning in particular those conditions where the Bromus plant does not start wilting owing to lack of water. This is the case in particular when the plant is supplied with such an amount of water within the first 4 weeks after application of the herbicidal composition that it is capable of replacing the water lost by transpiration by water from the soil and wilting is prevented (see, for example, Scheffer/Schachtschnabel: Lehrbuch der Bodenkunde [Textbook of Pedology], Ferdinand Enke Verlag (Stuttgart), 11$^{th}$ Edition (1982), p. 171 et seq.). For controlling Bromus, in particular under very dry conditions, it is preferred that the herbicidal compositions additionally comprise a surfactant b) which is not a silicone surfactant, and/or a humectant c), besides the compound of the formula (II') and/or its salts.

In addition, the herbicidal compositions may additionally comprise further agrochemical active substances (for example herbicides, insecticides, fungicides, safeners). Thus, in a preferred embodiment, for example, active substances of the formula (II') and/or their salts can be combined with other, different active substances of the formula (II) and/or their salts, for example
mesosulfuron-methyl+iodosulfuron-methyl,
mesosulfuron-methyl+iodosulfuron-methyl-sodium,
mesosulfuron-methyl+foramsulfuron,
mesosulfuron-methyl+foramsulfuron-sodium,
mesosulfuron-methyl-sodium+iodosulfuron-methyl,
mesosulfuron-methyl-sodium+iodosulfuron-methyl-sodium,
mesosulfuron-methyl-sodium+foramsulfuron,
mesosulfuron-methyl-sodium+foramsulfuron-sodium,
foramsulfuron+iodosulfuron-methyl,
foramsulfuron+iodosulfuron-methyl-sodium,
foramsulfuron-sodium+iodosulfuron-methyl,
foramsulfuron-sodium+iodosulfuron-methyl-sodium.

The herbicidal active substances of the formula (II') and/or their salts and their mixtures, for example the abovementioned active substance mixtures of active substances of the formula (II') and/or their salts with other, different active substances of the formula (II) and/or their salts can preferably be combined with a $C_8$–$C_{20}$-alkyl polyglycol ether sulfate such as sodium $C_{12}/C_{14}$-fatty alcohol diglycol ether sulfate (tradename for example Genapol® LRO, Clariant GmbH) as component b) and/or a lactic acid derivative such as sodium lactate as component c). In addition, preferably one or more safeners may be present, in particular the safeners mefenpyr-diethyl (S1-1), cloquintocet-mexyl (S2-1) and isoxadifen-ethyl (S3-1).

What has been said above for the statements on the herbicidal compositions according to claim 1 also applies analogously to the herbicidal compositions of this further embodiment of the present invention.

The use examples which follow illustrate the invention and have no limiting character whatsoever.

A. PREPARATION OF THE SPRAY MIXTURES

The individual components herbicide, surfactant and humectant with regard to type and application rate as stated in Tables 1–4 were added with stirring to a water application rate of 300 l/ha so that a homogeneous spray mixture was formed. The active substances rimsulfuron and nicosulfuron in the commercially available formulations Cato® WG25 (Du Pont) and Motivell® (BASF) were used for this purpose, respectively. Iodosulfuron-methyl-sodium and mesosulfuron-methyl were added in each case as 20 percent water-dispersible powders. Foramsulfuron was used as 50 percent water-dispersible granules. The surfactants used were Genapol® LRO as 70 percent paste (Clariant) and Synperonic® A7 (Unichema). Humectants employed were sodium lactate as 50 percent aqueous solution (Merck KGaA, Darmstadt) and propylene glycol (Clariant). The spray application was carried out as described in the examples section.

B. BIOLOGICAL EXAMPLES

The abbreviations used hereinbelow denote:

| | |
|---|---|
| g a.i./ha | grams of active substance/hectare |
| AVEFA Avena fatua | ALOMY Alopecurus myosuroides |
| BROTE Bromus tectorum | DIGSA Digitaria adscendens |
| ECHCG Echinochloa crus-galli | LOLMU Lolium multiflorum |

Visual scoring was carried out using a percentage scale of 0%=no damage to 100%=all plants dead.

Example B.1

Seeds of the harmful plants AVEFA and LOLMU were sown in a sandy loam soil in round pots type 13 in a controlled-environment cabinet and watered slightly. During the entire experiment period, the substrate only received minimal irrigation. A daytime temperature of 18° C. and a nighttime temperature of 16° C. was adhered to, a uniform day length of 16 hours being achieved by additional illumination with sodium vapor lamps (approx. 7000 lux). The relative atmospheric humidity was 50%. Four weeks after sowing, the plants were treated on a laboratory spray conveyor with spray mixtures of components mesosulfuron-methyl (A1), sodium lactate and Genapol® LRO, which spray mixtures had been prepared in accordance with Example A. The water application rate for the spray application of the preparations was 300 l/ha. After the treatment, the plants were returned to the controlled-environment cabinet. Visual scoring 14 days after the application gave the results shown in Table 1.

TABLE 1

| | Action [%] against harmful plants | | |
|---|---|---|---|
| Components | G a.i./ha | AVEFA | LOLMU |
| A1 | 60 | 10 | 10 |
| A1 + | 60 | 20 | 50 |
| Genapol ® LRO | 324 | | |
| A1 + | 60 | 70 | 60 |
| Genapol ® LRO + | 324 | | |
| sodium lactate | 150 | | |

Example B.2

Seeds of the harmful plants LOLMU, ALOMY, AVEFA, ECHCG and DIGSA were sown in a sandy loam soil in round pots type 7 in a greenhouse and watered slightly. A daytime temperature of 22 to 24° C. and a nighttime temperature of 16 to 18° C. was adhered to, a uniform day length of 16 hours being achieved by additional illumination with sodium vapor lamps (approx. 7000 lux). The relative atmospheric humidity was 60 to 80%. Two weeks after sowing, the plants were treated on a laboratory spray conveyor with the spray mixtures of rimsulfuron (A2), nicosulfuron (A3), iodosulfuron-methyl sodium (A4) and foramsulfuron (A5) and of combinations of A2, A3, A4 and A5 with Genapol® LRO and sodium lactate, the spray mixtures being prepared as in Example A. The water application rate for the spray application of the preparations was 300 l/ha. After the treatment, the plants were returned to the greenhouse. Visual scoring 28 days after the application gave the results shown in Table 2.

TABLE 2

| | Action [%] against harmful plants | | | | |
|---|---|---|---|---|---|
| Components | g a.i./ha | LOLMU | ALOMY | AVEFA | ECHCG | DIGSA |
| A2 | 5 | 60 | 70 | 0 | 10 | 30 |
| A2 + | 5 | 98 | 90 | 85 | 85 | 70 |
| Genapol ® LRO + | | | | | | |
| sodium lactate | | | | | | |
| A3 | 20 | — | 0 | 0 | 0 | — |
| A3 + | 20 | — | 60 | 30 | 5 | — |
| Genapol ® LRO + | | | | | | |
| sodium lactate | | | | | | |
| A4 | 20 | 60 | 50 | 60 | 70 | 30 |
| A4 + | 20 | 65 | 70 | 95 | 80 | 40 |
| Genapol ® LRO + | | | | | | |
| sodium lactate | | | | | | |

TABLE 2-continued

| Components | g a.i./ha | Action [%] against harmful plants | | | | |
|---|---|---|---|---|---|---|
| | | LOLMU | ALOMY | AVEFA | ECHCG | DIGSA |
| A5 | 20 | 50 | 70 | 60 | 30 | 0 |
| A5 + Genapol ® LRO + sodium lactate | 20 | 70 | 80 | 98 | 45 | 30 |

Example B.3

Seeds of the harmful plant BROTE were sown in a sandy loam soil in round pots type 13 in the open and watered slightly. During the entire experimental period, the substrate only received minimal irrigation. Four weeks after sowing, the plants were treated on a laboratory spray conveyor with spray mixtures of components mesosulfuron-methyl (A1), Genapol® LRO and sodium lactate, A1, Synperonic®A7 and sodium lactate and A1, Genapol® LRO and propylene glycol, the spray mixtures being prepared as in Example A. The water application rate for the spray application of the preparations was 300 l/ha. After the treatment, the plants were returned to the open. Visual scoring 28 days after application gave the results shown in Table 3.

TABLE 3

| Components | g a.i./ha | Action [%] against harmful plants |
|---|---|---|
| | | BROTE |
| A1 | 10 | 12.5 |
| A1 + Genapol ® LRO | 10 300 | 12.5 |
| A1 + Genapol ® LRO + sodium lactate | 10 300 300 | 42.5 |
| A1 + Synperonic ® A7 | 10 300 | 10 |
| A1 + Synperonic ® A7 + sodium lactate | 10 300 300 | 17.5 |
| A1 + Genapol ® LRO + propylene glycol | 10 300 300 | 27.5 |

Example B.4

Seeds of the harmful plant BROTE were sown in a sandy loam soil in round pots type 7 in a greenhouse and watered slightly. A daytime temperature of 22 to 24° C. and a nighttime temperature of 16 to 18° C. was adhered to, a uniform day length of 16 hours being achieved by additional illumination with sodium vapor lamps (approx. 7000 lux). The relative atmospheric humidity was 60 to 80%. Two weeks after sowing, the plants were treated on a laboratory spray conveyor using an oil dispersion containing 1.5% by weight mesosulfuron-methyl (A1) and 4.5% by weight mefenpyr-diethyl (S1-1) and combinations of the oil dispersion containing 1.5% by weight of mesosulfuron-methyl and 4.5% by weight of mefenpyr-diethyl with Genapol® LRO (300 g Genapol® LRO/ha). The water application rate for the spray application of the preparations was 300 l/ha. After the treatment, the plants were returned to the greenhouse. Visual scoring 28 days after the application gave the results shown in Table 4.

TABLE 4

| Components | g a.i./ha | Action [%] against harmful plants |
|---|---|---|
| | | BROTE |
| A1* | 7.5 | 80 |
| | 11 | 87.5 |
| A1* + Genapol ® LRO | 7.5 | 85 |
| | 11 | 90 |

A1*: mesosulfuron-methyl (A1) + mefenpyr-diethyl (S1-1)

We claim:

1. A herbicidal composition comprising a) one or more herbicidal active substances, b) one or more surfactants other than silicone surfactants, and c) one or more humectants selected from the group consisting of lactic acid and lactic acid derivatives.

2. A herbicidal composition as claimed in claim 1, additionally comprising one or more further components from the group consisting of agrochemical active substances, additives conventionally used in the art of crop protection, and formulation auxiliaries.

3. A herbicidal composition as claimed in claim 1, comprising, as component a), a sulfonylurea.

4. The herbicidal composition according to claim 3 wherein the sulfonylurea herbicide is selected from the group consisting of mesosulfuron-methyl, rimsulfuron, nicosulfuron, iodosulfuron-methyl sodium, and foramsulfuron.

5. The herbicidal composition according to claim 4, wherein the surfactant is a $C_8$–$C_{20}$ alkyl polyglycol.

6. The herbicidal composition according to claim 5, wherein the humectant is sodium lactate.

7. A method for the preparation of a herbicidal composition defined as in claim 1, wherein components a), b) and c) are mixed.

8. A method as claimed in claim 7, wherein component a), b) and c) are mixed by the tank mix method.

9. A method of controlling harmful plants, wherein the herbicidal composition defined as in claim 1 is applied pre-emergence, post-emergence or pre- and post-emergence to the plants, plant parts, plant seeds or the area on which the plants grow.

10. The method according to claim 9, wherein the harmful plants are controlled selectively.

11. The method according to claim 9, wherein the area on which plants grow is an area under cultivation.

12. A herbicidal composition comprising
a) at least one compound of the formula

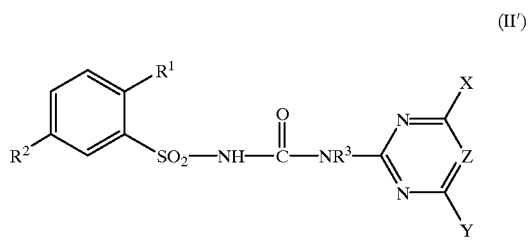

(II')

or a salt thereof
in which
$R^1$ is CO—($C_1$–$C_4$-alkoxy),
$R^2$ is $CH_2$—$NHR^e$, where $R^e$ is a acyl radical,
$R^3$ is H or $C_1$–$C_4$-alkyl,
X and Y independently of one another are identical or different and are $C_1$–$C_6$-alkyl, $C_1$–$C_6$ alkoxy and $C_1$–$C_4$-alkylthio, where each of the three abovementioned radicals is unsubstituted or substituted by one or more radicals selected from the group consisting of halogen, $C_1$–$C_4$-alkoxy and $C_1$–$C_4$-alkylthio, or $C_3$–$C_6$-cycloalkyl, $C_2$–$C_6$-alkenyl, $C_2$–$C_6$-alkynyl, $C_3$–$C_6$-alkenyloxy or $C_3$–$C_6$-alkynyloxy, and
Z is CH or N,
b) at least one surfactant other than a silicone surfactant, and
c) at least one humectant selected from the group consisting of lactic acid, and lactic acid derivatives.

13. The herbicidal composition according to claim 12, wherein $R^e$ is $C_1$–$C_4$ alkylsulfonyl.

14. The herbicidal composition according to claim 12, wherein X and Y independently from one another are $C_1$–$C_4$ alkyl or $C_1$–$C_4$ alkoxy.

15. The herbicidal composition according to claim 12 wherein the surfactant is a $C_8$–$C_{20}$ alkyl polyglycol.

16. The herbicidal composition according to claim 12, wherein the humectant is sodium lactate.

17. The herbicidal composition according to claim 12, which further comprises at least one agrochemical active substance.

18. A method for controlling the growth of Bromus plants which comprises applying a composition according to claim 12 pre-emergently, post-emergently or pre- and post-emergently to the Bromus plants, plant parts, plant seeds or to an area where the Bromus plants grow.

19. The method according to claim 18 wherein the area where the Bromus plants grow is an area under cultivation.

20. The method according to claim 18 wherein the Bromus plants are controlled selectively.

21. A method for controlling the growth of Bromus plants which comprises applying a composition comprising at least one compound of the formula

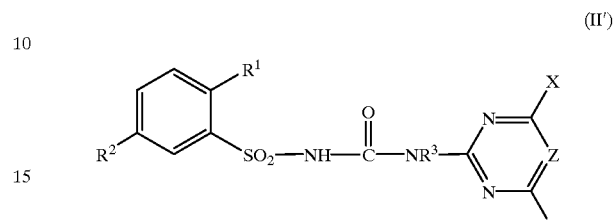

(II')

or a salt thereof
in which
$R^1$ is CO—($C_1$–$C_4$-alkoxy),
$R^2$ is $CH_2$—$NHR^e$, where $R^e$ is a acyl radical,
$R^3$ is H or $C_1$–$C_4$-alkyl,
X and Y independently of one another are identical or different and are $C_1$–$C_6$-alkyl, $C_1$–$C_6$alkoxy and $C_1$–$C_4$-alkylthio, where each of the three abovementioned radicals is unsubstituted or substituted by one or more radicals selected from the group consisting of halogen, $C_1$–$C_4$-alkoxy and $C_1$–$C_4$-alkylthio, or $C_3$–$C_6$-cycloalkyl, $C_2$–$C_6$-alkenyl, $C_2$–$C_6$-alkynyl, $C_3$–$C_6$-alkenyloxy or $C_3$–$C_6$-alkynyloxy, and
Z is CH or N
pre-emergently, post-emergently or pre- and post-emergently to the Bromus plants, plant parts, plant seeds or to an area where the Bromus plants grow.

22. The method according to claim 21 wherein the area where the Bromus plants grow is an area under cultivation.

23. The method according to claim 21 wherein the Bromus plants are controlled selectively.

24. The method according to claim 21 wherein the composition further comprises one or more surfactants other than silicone surfactants andlor one or more humectants.

25. The method according to claim 21 wherein the composition further comprises one or more agrochemical agents.

* * * * *